(12) United States Patent
Park et al.

(10) Patent No.: US 12,115,516 B2
(45) Date of Patent: Oct. 15, 2024

(54) METHOD FOR MANUFACTURING CARBOXYMETHYL CELLULOSE PARTICLES, CARBOXYMETHYL CELLULOSE PARTICLES MANUFACTURED THEREBY, AND ABSORBENT ARTICLE COMPRISING SAME

(71) Applicant: LOTTE FINE CHEMICAL CO., LTD., Ulsan (KR)

(72) Inventors: Soo Hee Park, Ulsan (KR); Hee Soo Kim, Hwaseong-Si (KR); Sang Yob Kim, Goyang-Si (KR)

(73) Assignee: LOTTE FINE CHEMICAL CO., LTD., Ulsan (KR)

(*) Notice: Subject to any disclaimer, the term of this patent is extended or adjusted under 35 U.S.C. 154(b) by 448 days.

(21) Appl. No.: 17/436,147

(22) PCT Filed: Mar. 4, 2020

(86) PCT No.: PCT/KR2020/003085
§ 371 (c)(1),
(2) Date: Sep. 3, 2021

(87) PCT Pub. No.: WO2020/180117
PCT Pub. Date: Sep. 10, 2020

(65) Prior Publication Data
US 2022/0126269 A1    Apr. 28, 2022

(30) Foreign Application Priority Data

Mar. 4, 2019  (KR) .................. 10-2019-0024793
Mar. 4, 2019  (KR) .................. 10-2019-0024794

(51) Int. Cl.
*B01J 20/24*    (2006.01)
*A61L 15/28*    (2006.01)
(Continued)

(52) U.S. Cl.
CPC .............. *B01J 20/24* (2013.01); *A61L 15/28* (2013.01); *A61L 15/60* (2013.01);
(Continued)

(58) Field of Classification Search
CPC ........ A61L 15/28; A61L 15/425; A61L 15/60; B01J 20/24; B01J 20/28011;
(Continued)

(56) References Cited

FOREIGN PATENT DOCUMENTS

| CN | 108884234 A | 11/2018 |
|---|---|---|
| JP | 2005263858 A | 9/2005 |

(Continued)

OTHER PUBLICATIONS

Machine translation of KR20190080165. (Year: 2019).*
(Continued)

*Primary Examiner* — Brian A McCaig
(74) *Attorney, Agent, or Firm* — Osha Bergman Watanabe & Burton LLP

(57) ABSTRACT

The present disclosure relates to a method for manufacturing carboxymethyl cellulose particles, cellulose inducer particles manufactured by the method, and an absorbent article comprising same. The method comprises: (1) a step of obtaining alkalized cellulose by reacting a cellulose raw material with an alkalizer; (2) a step of obtaining carboxymethyl cellulose by reacting the alkalized cellulose with a carboxy methylating agent; (3) a primary cross-linking step of obtaining a slurry-phase carboxymethyl cellulose cross-linked body by reacting the carboxymethyl cellulose with a core cross-linker; (4) a step of washing and dehydrating after filtering the slurry-phase carboxymethyl cellulose cross-linked body; (5) a secondary cross-linking step of obtaining carboxymethyl cellulose having a core-shell structure by reacting the carboxymethyl cellulose cross-linked body having undergone Step (4) with a surface cross-linker; and (6)
(Continued)

a step of obtaining carboxymethyl cellulose particles having a core-shell structure by drying and pulverizing the carboxymethyl cellulose having a core-shell structure.

24 Claims, 5 Drawing Sheets

(51) Int. Cl.
*A61L 15/60* (2006.01)
*B01J 20/28* (2006.01)
*B01J 20/30* (2006.01)
*C08B 1/08* (2006.01)
*C08B 11/12* (2006.01)
*C08B 15/00* (2006.01)
*C08J 3/12* (2006.01)
*C08J 3/24* (2006.01)

(52) U.S. Cl.
CPC ... *B01J 20/28011* (2013.01); *B01J 20/28016* (2013.01); *B01J 20/3021* (2013.01); *B01J 20/3071* (2013.01); *B01J 20/3085* (2013.01); *C08B 1/08* (2013.01); *C08B 11/12* (2013.01); *C08B 15/005* (2013.01); *C08J 3/126* (2013.01); *C08J 3/245* (2013.01); *B01J 2220/44* (2013.01); *B01J 2220/68* (2013.01); *C08J 2301/28* (2013.01)

(58) Field of Classification Search
CPC ............. B01J 20/28016; B01J 20/3021; B01J 20/3071; B01J 20/3085; B01J 2220/44; B01J 2220/68; C08B 1/08; C08B 11/12; C08B 15/005; C08J 3/12; C08J 3/126; C08J 3/243; C08J 3/245; C08J 9/08; C08J 9/16; C08J 2203/02; C08J 2301/28
See application file for complete search history.

(56) References Cited

FOREIGN PATENT DOCUMENTS

| | | | |
|---|---|---|---|
| JP | 2008-503600 | A | 2/2008 |
| JP | 2012077157 | A | 4/2012 |
| JP | 2015-178099 | A | 10/2015 |
| JP | 2016053144 | A | 4/2016 |
| KR | 20010105311 | A | 11/2001 |
| KR | 20180066723 | A | 6/2018 |
| KR | 20180067940 | A | 6/2018 |
| KR | 20180071852 | A | 6/2018 |
| KR | 20190080165 | A * | 7/2019 .............. C08J 3/245 |

OTHER PUBLICATIONS

International Search Report issued in International Application No. PCT/KR2020/003085 dated Jun. 30, 2020 (2 pages).
Written Opinion issued in International Application No. PCT/KR2020/003085 dated Jun. 30, 2020 (5 pages).
Extended European Search Report issued in European Application No. 20766009.3, mailed on Nov. 24, 2022 (10 pages).
Jockusch et al.; "Photoinduced Surface Crosslinking of Superabsorbant Polymer Particles;" Journal of Applied Polymer Science; vol. 111; 2009; pp. 2163-2170 (8 pages).
Wright et al.; "Biological Variation of Routine Haematology Biochemistry Measurands in the Horse;" Equine Veterinary Jornal; Journal 51; 2019; pp. 384-390 (7 pages).

* cited by examiner

[Figure 1]

[Figure 2]

[Figure 3]

[Figure 4]
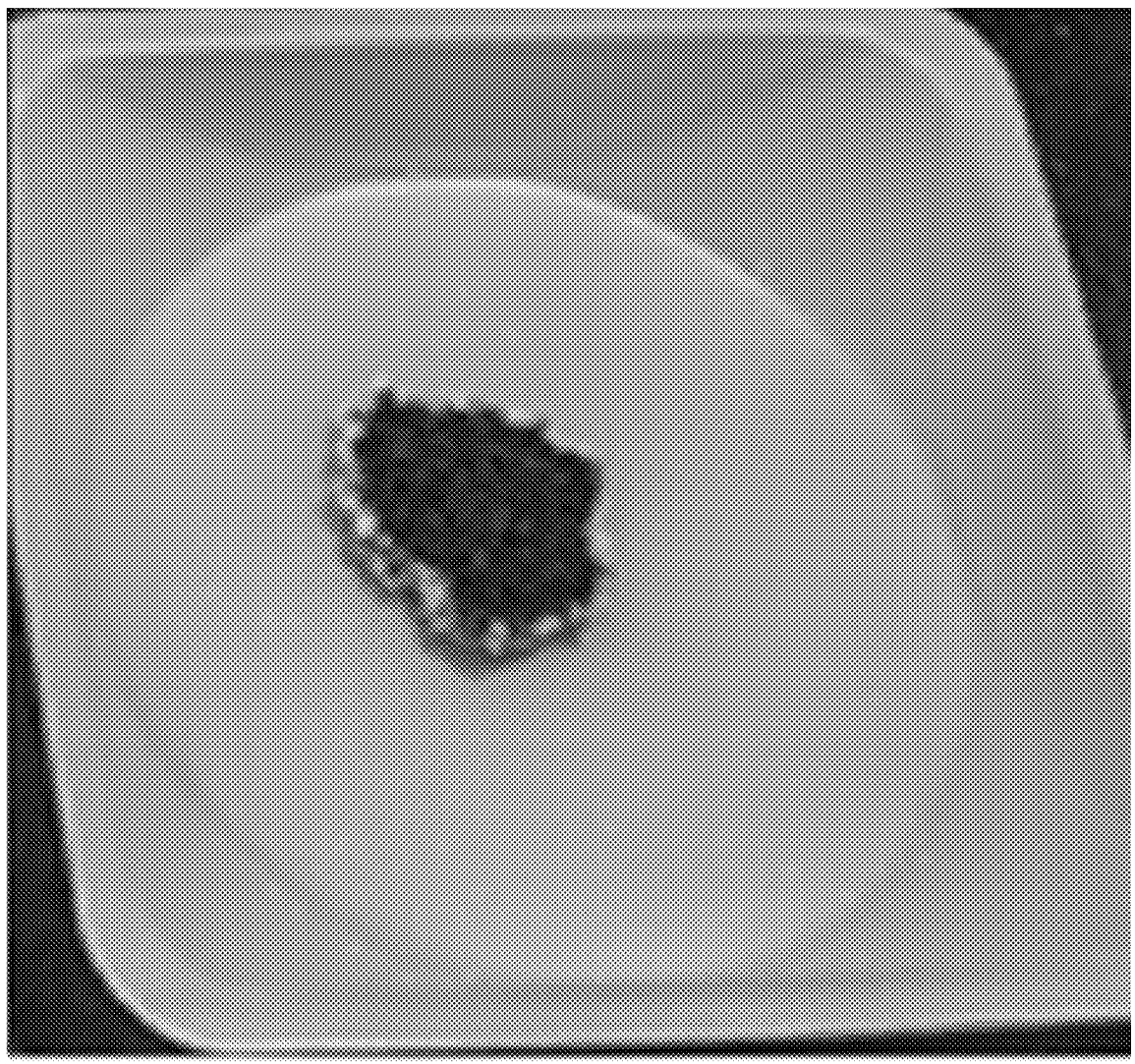

[Figure 5]
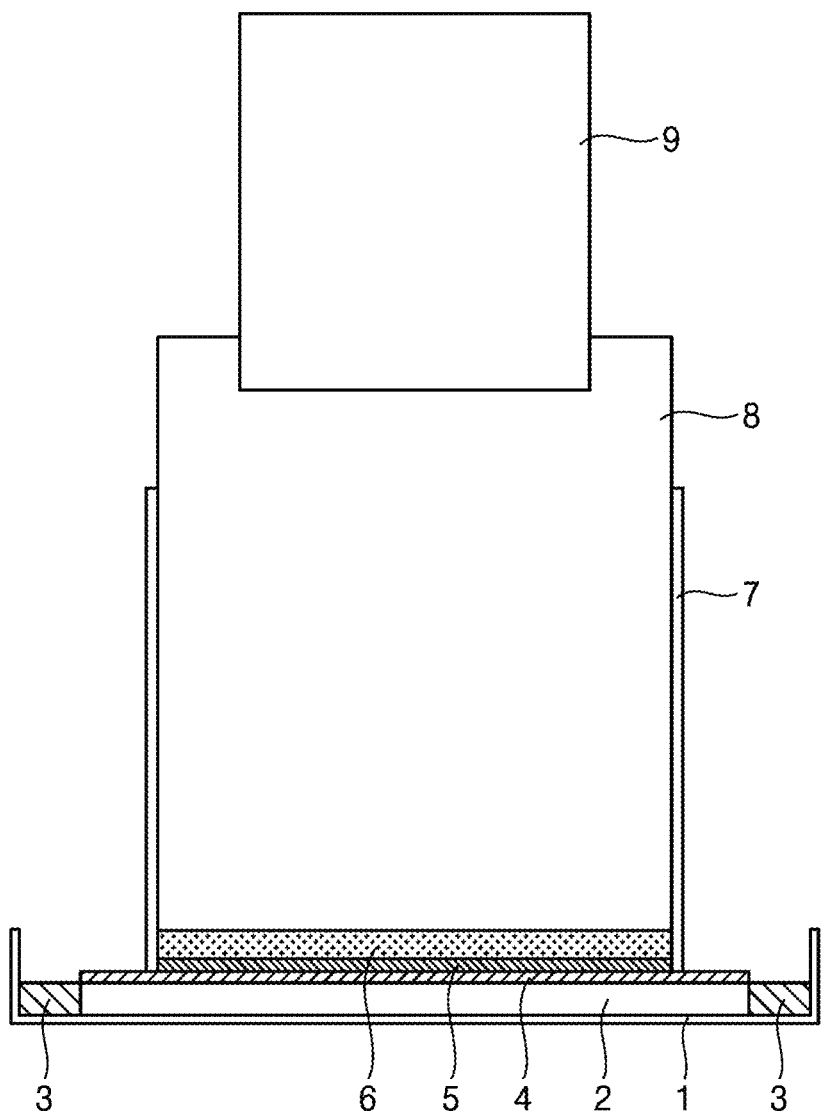

METHOD FOR MANUFACTURING CARBOXYMETHYL CELLULOSE PARTICLES, CARBOXYMETHYL CELLULOSE PARTICLES MANUFACTURED THEREBY, AND ABSORBENT ARTICLE COMPRISING SAME

TECHNICAL FIELD

The present invention relates to a method for manufacturing carboxymethyl cellulose (hereinafter referred to as "CMC") particles, CMC particles manufactured by the method, and an absorbent article including the same, and more particularly, to a method for manufacturing CMC particles, which includes: reacting a CMC cross-linked body having undergone a core cross-linking step with a surface cross-linker to obtain CMC having a core-shell structure, CMC particles manufactured by the method, and an absorbent article including the same.

BACKGROUND ART

A superabsorbent polymer (hereinafter referred to as "SAP") is a functional material that may absorb water in an amount several tens to several thousands of times its own weight, and thus has been widely used as a material for absorbent articles, such as hygiene products, for example, diapers for children, feminine sanitary pads, adult incontinence products, or the like; pet supplies such as defecation pads and the like; medical absorbents; waterproofing materials for civil engineering and construction; sheets for raising seedlings; freshness retainers used in the field of food distribution; and the like.

Because the SAP is mainly used for one-time use, it should be easy to manufacture and inexpensive, and it has crucial physical properties such as an absorbing ability to absorb moisture from a substrate including an aqueous liquid, permeability, swollen gel strength, and the like.

In the related art, acrylic absorbent resins have been commonly used as such an SAP due to high absorbability and low process cost. However, an acrylic absorbent resin is a material obtained in the oil industry, and has a drawback in that it causes erythema or itching in the body parts which have come into contact with diapers or hygiene products for a long time when it is applied to the diapers or the hygiene products because it shows toxicity due to the presence of residual monomers. Therefore, research has been conducted to prepare CMC derived from cellulose, which is a natural vegetable substance, into superabsorbent particles and apply the superabsorbent particles to absorbent products.

As such a conventional method, Patent Document 1 (Korean Patent Laid-Open Publication No. 2001-0105311) discloses a method for manufacturing a superabsorbent polysaccharide derivative, which includes: (a) cross-linking one or more polysaccharides (such as CMC and the like) containing an acid group with a cross-linker to form a gel; (b), optionally, adjusting a pH of the polysaccharides to a range of pH 3.5 to pH 5.5; (c) pulverizing the acidified polysaccharide gel; and (d) drying the pulverized polysaccharides at a high temperature.

Patent Document 1 discloses that the superabsorbent polysaccharide derivative may be used to absorb a liquid composed of body fluids containing various salts and non-ionic materials, and is particularly suitable for manufacturing absorbent hygiene articles such as diapers, sanitary napkins, and the like. In fact, the superabsorbent polysaccharide derivative has been used as an absorbent material used for urine-absorbing diapers. However, the superabsorbent polysaccharide derivative may not applied to feminine products for absorbing blood because it has relatively low blood absorbability. This is because the physical properties of menstrual blood are highly different from those of urine. Specifically, because the menstrual blood includes water, salts, proteins, cells, and the like, it has a high viscosity and a very slow diffusion rate, compared to urine. Also, a large cell mass and the like included in blood are not absorbed into a conventional SAP such as the superabsorbent polysaccharide derivative, and form a film on a surface of the conventional SAP to prevent blood absorption.

As a method designed to solve this problem, Patent Document 2 (Japanese Patent Laid-Open Publication No. 2005-263858) discloses a method for manufacturing an absorbent material, which includes: (i) providing an aqueous solution including polyvalent metal ions and a surfactant, (ii) adding a cellulose derivative and/or alginic acid or salts thereof to the aqueous solution, followed by cross-linking the resulting mixture and simultaneously swelling and hydrating the mixture to form a gel, (iii) allowing the gel of the cross-linked body obtained in Step (ii) to come into contact with a hydrophilic volatile solvent to dehydrate the gel, and (iv) drying the gel. In this case, the method for manufacturing an absorbent material further includes: treating the solids obtained in Step (iii) or (iv) with a surface cross-linker.

Looking at embodiments of Patent Document 2, a CMC powder is used as the cellulose derivative and/or alginic acid or salts thereof, and the CMC powder is added to the aqueous solution provided in Step (i) to swell and cross-link the mixture to obtain a gel. However, according to the method, the CMC powder has a high viscosity as it is swollen by suddenly absorbing water at the beginning of Step (ii) of obtaining the cross-linked gel. Therefore, irregular non-uniform cross-linking reaction may occur. Considering wearing comfort when the absorbent material is applied to feminine sanitary pads, adult incontinence products, or the like, there is also still a need for improvement of blood absorbency and retention capacity of the absorbent material. In addition, because the absorbency under load used to measure a degree of absorption of physiological saline (or a NaCl solution) under pressure is a factor that may affect wearing comfort, there is also a need for improvement of the absorbency under load.

RELATED-ART DOCUMENTS

Patent Documents

Patent Document 1: KR1020010105311 A
Patent Document 2: JP2005263858 A

DISCLOSURE

Technical Problem

The present invention is designed to solve the problems of the related art, and thus it is an object of the present disclosure to provide a method for manufacturing CMC particles having excellent blood absorbency, centrifuge retention capacity (CRC), and absorbency under load (AUL), wherein the method includes: reacting a CMC cross-linked body undergoing a core cross-linking step with a surface cross-linker to obtain CMC having a core-shell structure.

It is another object of the present disclosure to provide CMC particles manufactured by the method, and an absorbent article including the same.

Technical Solution

According to an aspect of the present invention, there is provided a method for manufacturing CMC particles, which includes: (1) a step of obtaining alkalized cellulose by reacting a cellulose raw material with an alkalizer; (2) a step of obtaining CMC by reacting the alkalized cellulose with a carboxy methylating agent; (3) a primary cross-linking step of obtaining a slurry-phase carboxymethyl cellulose cross-linked body by reacting the carboxymethyl cellulose with a core cross-linker; (4) a step of washing and dehydrating after filtering the slurry-phase CMC cross-linked body; (5) a secondary cross-linking step of obtaining CMC having a core-shell structure by reacting the CMC cross-linked body having undergone Step (4) with a surface cross-linker; and (6) a step of obtaining CMC particles having a core-shell structure by drying and pulverizing the CMC having a core-shell structure.

According to another aspect of the present invention, there are provided CMC particles manufactured by the method for manufacturing CMC particles.

According to still another aspect of the present invention, there is provided an absorbent article including the CMC particles manufactured by the method for manufacturing CMC particles.

Advantageous Effects

According to the present invention, modified CMC particles having superabsorbability can be manufactured by a method which includes: obtaining CMC having a core-shell structure by reacting a CMC cross-linked body having undergone a core cross-linking step with a surface cross-linker.

The CMC particles thus manufactured can have excellent gel strength and AUL due to surface cross-linking, and can show excellent blood absorbency due to improved bulk density obtained in a secondary cross-linking step. In addition, according to the present invention, CMC particles having excellent CRC, which represents a retention capacity measured under severe conditions, for example, a retention amount of physiological saline measured after centrifugation, can be provided. Therefore, the CMC particles according to the present invention can be preferably used for feminine products for absorbing blood.

According to the present invention, because the gelation of CMC does not proceed during a core cross-linking process, problems regarding the non-uniform cross-linking caused by high viscosity in this process can also be resolved.

DESCRIPTION OF DRAWINGS

FIG. 1 is an image of CMC particles manufactured in Example 1 to which blood is applied.

FIG. 2 is an image of the CMC particles after the CMC particles which does not contact with blood are swept off from the Petri dish shown in FIG. 1.

FIG. 3 is an image of CMC particles manufactured in Example 8 to which blood is applied.

FIG. 4 is an image of the CMC particles after the CMC particles which does not contact with blood are swept off from the Petri dish shown in FIG. 3.

FIG. 5 is a device for measuring AUL of the CMC particles.

BEST MODE

Hereinafter, the present invention will be described in detail.

Throughout this specification, when any certain part is said to "include" any component, this means that it may further include other components, rather than excluding other components unless otherwise stated.

In this specification, the term "core cross-linking" refers to a cross-linking reaction by which a main chain of CMC is formed through a reaction of CMC with a cross-linker. In this case, the cross-linker used herein refers to a "core cross-linker," and the reaction of CMC with the core cross-linker refers to a "core cross-linking reaction."

In this specification, the term "surface cross-linking (or a shell cross-linking)" refers to a cross-linking reaction by which a main chain of CMC is formed on a surface of the CMC cross-linked body through a reaction of the CMC cross-linked body having core cross-linking with a cross-linker. In this case, the cross-linker used herein refers to a "surface cross-linker (or a shell cross-linker)," and the reaction of the CMC cross-linked body with the surface cross-linker refers to a "surface cross-linking reaction."

One embodiment of the present invention provides a method for manufacturing CMC particles includes: (1) obtaining alkalized cellulose by reacting a cellulose raw material with an alkalizer; (2) obtaining CMC by reacting the alkalized cellulose with a carboxy methylating agent; (3) a primary cross-linking step of obtaining a slurry-phase CMC cross-linked body by reacting the CMC with a core cross-linker; (4) a step of washing and dehydrating after filtering the slurry-phase CMC cross-linked body; (5) a secondary cross-linking step of obtaining CMC having a core-shell structure by reacting the CMC cross-linked body having undergone Step (4) with a surface cross-linker; and (6) a step of obtaining CMC particles having a core-shell structure by drying and pulverizing the CMC having a core-shell structure.

Hereinafter, respective steps of the method for manufacturing CMC particles according to the present invention will be described in detail.

(1) Obtaining Alkalized Cellulose (Alkalization Step)

This step is a step of obtaining alkalized cellulose by reacting a cellulose raw material with an alkalizer.

Conventional types of pulp commonly used in the related art may be used as the cellulose raw material without any limitation on the length of the pulp. Specifically, pulp having a length of 1 μm or more and less than 8 mm may be used. More specifically, pulp having a length of 0.15 mm or more and 0.5 mm or less may be used. Even more specifically, the cellulose raw material may be prepared by cutting one or more types of pulp selected from the group consisting of raw cotton, linter, and wood into a length of 0.15 mm or more and 0.5 mm or less. When the cellulose raw material thus cut is used, a uniform reaction may be possible because the entanglement of a stirrer with the cellulose raw material is reduced and lumping of fine pulp is suppressed, a working time may be reduced, and workability and fluidity may be secured to improve productivity. In this case, it is possible to reduce manufacturing costs by 30% or more, compared to when the cellulose raw material is used without having undergone a cutting process.

The obtaining of the alkalized cellulose may be performed using a conventional method commonly used in the art. For example, a method for converting cellulose into alkalized cellulose, which includes: introducing a cellulose raw material and a reaction solvent into a reactor, adding an alkalizer hereto, and reacting the resulting mixture while stirring at a temperature of 20° C. or higher and 30° C. or lower and at a speed of 100 rpm or more and 200 rpm or less for a time period of 90 minutes or more and 150 minutes or less, may be used.

The reaction solvent may include one or more selected from the group consisting of water, acetone, isopropyl alcohol, tert-butyl alcohol, and dimethyl ether. In this case, a use amount of the reaction solvent may be greater than or equal to 50 parts by weight and less than or equal to 2,000 parts by weight, based on 100 parts by weight of the cellulose raw material.

The alkalizer may include an alkali metal hydroxide. For example, the alkalizer may include one or more selected from the group consisting of sodium hydroxide, potassium hydroxide, and lithium hydroxide, and may be used in the form of an aqueous solution. An addition amount of the alkalizer may be greater than or equal to 5 parts by weight and less than or equal to 600 parts by weight, based on 100 parts by weight of the cellulose raw material. When the addition amount of the alkalizer falls within the above range, a carboxymethyl group may be uniformly substituted throughout the cellulose in Step (2) to be described below. In this case, CMC having a desired degree of substitution may be obtained due to increased reactivity of the carboxy methylating agent.

The purpose of adding the alkalizer is to weaken a crystal structure of cellulose to allow the cellulose to easily react with the carboxy methylating agent to be described below. That is, the alkalizer serves to promote a reaction of the cellulose with the carboxy methylating agent. In this way, the alkalized cellulose should be stirred at room temperature (20° C. to 30° C.) for a certain time so the crystal structure of cellulose may be uniformly weakened.

(2) Obtaining CMC (Carboxy Methylation Step)

This step is a step of obtaining CMC by reacting the alkalized cellulose obtained in Step (1) with a carboxy methylating agent.

The obtaining of CMC may be performed using a conventional method commonly used in the art. For example, a method for reacting the alkalized cellulose with a carboxy methylating agent, which includes: introducing a carboxy methylating agent into a reactor containing the alkalized cellulose obtained in Step (1) and raising the temperature to allow a reaction, may be used.

According to one embodiment of the present invention, Step (2) may include: (2-1) a primary carboxy methylation step performed at 40° C. or higher and 55° C. or lower for 90 minutes or more and 150 minutes or less; and (2-2) a secondary carboxy methylation step performed at 65° C. or higher and 75° C. or lower for 30 minutes or more and 90 minutes or less.

Specifically, the carboxy methylating agent may include any one selected from chloroacetic acid, a chloroacetic acid sodium salt, and a mixture thereof, and may be used in the form of a mixed solution in which it is dissolved in a reaction solvent. In this case, the reaction solvent may include one or more selected from the group consisting of water, acetone, isopropyl alcohol, tert-butyl alcohol, and dimethyl ether.

According to one embodiment of the present invention, a degree of carboxymethyl group substitution (DS) of the CMC manufactured in Step (2) may be greater than or equal to 0.7 and less than or equal to 2.0, and a degree of polymerization (DP) of the CMC may be greater than or equal to 800 and less than or equal to 4,000. In this specification, the degree of carboxymethyl group substitution (DS) represents the average number of hydroxyl groups substituted with carboxymethyl groups per anhydrous glucose unit in cellulose molecules. In this case, when the degree of carboxymethyl group substitution (DS) falls within the above range, a uniform reaction may be preferably performed. Also, because the degree of polymerization of CMC is a factor that affects the viscosity of CMC, CMC particles having excellent bulk density may be manufactured when the degree of polymerization falls within the above range, which is desirable.

According to one embodiment of the present invention, before undergoing Step (3) as described below, the method for manufacturing CMC particles may further include: (2.5) neutralizing the CMC obtained in Step (2). The neutralization step may be performed according to a conventional method commonly used in the art. For example, the CMC may be neutralized by adding a neutralizing agent to the CMC. Here, all types of oxidizing agents may be used as the neutralizing agent. For example, nitric acid, acetic acid, hydrochloric acid, and the like may be mainly used as the neutralizing agent. In this case, these acids may be used in the form of an aqueous solution in which they are diluted to a concentration of 40% by weight or more and 99% by weight or less.

(3) Primary Cross-Linking Step (Core Cross-Linking Step)

This step is a step of obtaining a slurry-phase CMC cross-linked body by reacting the CMC obtained in Step (2) with a core cross-linker. Here, the slurry-phase refers to a liquid phase that has low fluidity and contains a high concentration of a suspended material (a CMC cross-linked body), and gelation does not proceed in this step.

Steps (1) to (3) may be continuously or discontinuously performed. For example, when Steps (1) to (3) are performed in the same reactor, the CMC in which a carboxy methylation reaction has been completed or is in progress may be present in the reactor having undergone Step (2). In this case, a core cross-linking reaction may be continuously performed by adding a core cross-linker to the CMC. That is, according to the present invention, a core cross-linker may be introduced into the reactor containing wet-type CMC without any separate drying or pulverization process after Step (2) (a carboxy methylation step), and the wet-type CMC itself takes part in the core cross-linking reaction to form a CMC cross-linked body. Core cross-linking may be formed in the main chain (backbone) of the CMC through a reaction of the wet-type CMC with the core cross-linker, thereby obtaining a slurry-phase CMC cross-linked body.

Meanwhile, when Steps (1) to (3) are discontinuously performed, the wet-type CMC may undergo a drying or pulverization process after Step (2). Then, the dry-type CMC undergoing this process, the core cross-linker, and the reaction solvent may be introduced into the reactor. Thereafter, core cross-linking may be formed in the main chain (backbone) of the CMC through a reaction of the CMC with the core cross-linker, thereby obtaining a slurry-phase CMC cross-linked body.

In this case, because a process is simple and economical, the case of continuously performing Steps (1) to (3) in the same reactor is preferable over the case of discontinuously performing Steps (1) to (3). The CMC subjected to the core cross-linking in this way may have dispersibility and absorbability when present in 0.9% saline.

According to one embodiment of the present invention, the core cross-linker may include one or more selected from the group consisting of an epoxy compound and a polyhydric alcohol. Specifically, examples of the epoxy compound may include epichlorohydrin, glycerol diglycidyl ether, polyethylene glycol diglycidyl ether, diethylene glycol diglycidyl ether, ethylene glycol diglycidyl ether, polypropylene glycol diglycidyl ether, tripropylene glycol diglycidyl ether, propylene glycol diglycidyl ether, glycidol, and the like, and examples of the polyhydric alcohol may include glycerin, glycerol, ethylene glycol, diethylene glycol, triethylene glycol, tetraethylene glycol, polyethylene glycol, propylene glycol, dipropylene glycol, polypropylene glycol, and the like.

According to one embodiment of the present invention, a content of the core cross-linker may be greater than or equal to 0.1 parts by weight and less than or equal to 40 parts by weight, based on 100 parts by weight of the cellulose raw material. When the content of the core cross-linker falls within the above range, the core cross-linker may exhibit excellent core cross-linking reaction efficiency and appropriate core cross-linking density. Therefore, the centrifuge retention capacity (CRC) of the finally provided CMC particles may be improved.

According to one embodiment of the present invention, Step (3) may be performed while stirring at 65° C. or higher and 75° C. or lower and at a speed of 100 rpm or higher and 300 rpm or less for 30 minutes or more and 90 minutes or less. When the reaction temperature, the reaction time, and the stirring speed fall within the above ranges, the core cross-linking may be performed without any gelation. In addition, the core cross-linking may be economical due to high cross-linking reaction efficiency relative to the input energy. Furthermore, Step (3) may be performed under the condition of pH 6 or more and pH 8 or less. In this case, it is easy to control a cross-linking reaction, and cross-linking efficiency may be improved.

(4) Step of Filtering, Washing, and Dehydrating

This step is a step of filtering the slurry-phase CMC cross-linked body obtained in Step (3), followed by washing and dehydrating.

Specifically, the slurry-phase CMC cross-linked body obtained in Step (3) may be discharged from the reactor, and then filtered according to a filtration method commonly known in the art. For example, the filtration used herein may include sieve filtration, suction filtration, ultrafiltration, filter pressing, and the like. Specifically, suction filtration may be used, but the present invention is not limited thereto.

According to one embodiment of the present invention, one or more selected from the group consisting of water and a hydrophilic volatile organic solvent may be used for the washing in Step (4). Specifically, an aqueous solution including the hydrophilic volatile organic solvent may be used. Specific examples of the hydrophilic volatile organic solvent may include lower alcohols such as methanol, ethanol, n-propyl alcohol, isopropyl alcohol, n-butyl alcohol, isobutyl alcohol, tert-butyl alcohol, and the like; ketones such as acetone, methyl ethyl ketone, and the like; ethers such as 1,4-dioxane, tetrahydrofuran, and the like; amides such as N,N-dimethylformamide, and the like; sulfoxides such as dimethyl sulfoxide, and the like, but the present invention is not limited thereto. More specifically, methanol, ethanol, or isopropyl alcohol may be used. When the CMC cross-linked body undergoes the washing process, impurities are removed, thereby obtaining a CMC cross-linked body having a purity of 99% or more.

(5) Secondary Cross-Linking Step (Surface Cross-Linking Step)

This step is a step of obtaining CMC having a core-shell structure by reacting the CMC cross-linked body having undergone Step (4) with a surface cross-linker.

According to one embodiment of the present invention, the surface cross-linker may include one or more selected from the group consisting of a polyhydric epoxy compound and a polyhydric alcohol. Specifically, examples of the epoxy compound may include epichlorohydrin, glycerol diglycidyl ether, polyethylene glycol diglycidyl ether, diethylene glycol diglycidyl ether, ethylene glycol diglycidyl ether, polypropylene glycol diglycidyl ether, tripropylene glycol diglycidyl ether, propylene glycol diglycidyl ether, glycidol and the like, and examples of the polyhydric alcohol may include glycerin, glycerol, ethylene glycol, diethylene glycol, triethylene glycol, tetraethylene glycol, polyethylene glycol, propylene glycol, dipropylene glycol, polypropylene glycol, and the like.

According to one embodiment of the present invention, a content of the surface cross-linker may be greater than or equal to 0.1 parts by weight and less than or equal to 40 parts by weigh, based on 100 parts by weight of the CMC cross-linked body having undergone Step (4). When the content of the surface cross-linker falls within the above range, CMC particles having excellent surface cross-linking reaction efficiency and good absorbency under load may be provided.

Meanwhile, in the method for manufacturing CMC particles according to the present invention, one method selected from the two following methods may be used in Step (5).

As the first method, Step (5) may be a secondary cross-linking step of obtaining porous CMC having a core-shell structure by reacting the CMC cross-linked body having undergone Step (4) with the surface cross-linker and a foaming agent. In this case, the foaming agent and the surface cross-linker may be in the form of a solution to react with the CMC cross-linked body. Specifically, in Step (5), a foaming agent solution and a surface cross-linker solution may be added to the CMC cross-linked body, or a mixed solution obtained by mixing a foaming agent solution and a surface cross-linker solution may be added to the CMC cross-linked body.

According to one embodiment of the present invention, the foaming agent may include a carbonate compound. Specifically, the foaming agent may include one or more carbonate compounds selected from the group consisting of magnesium carbonate, calcium carbonate, sodium bicarbonate, and potassium bicarbonate. As a water-soluble compound, the foaming agent may be added in the form of an aqueous solution.

According to one embodiment of the present invention, a content of the foaming agent may be greater than or equal to 0.03 parts by weight and less than or equal to 20 parts by weight, specifically greater than or equal to 0.3 parts by weight and less than or equal to 15 parts by weight, based on 100 parts by weight of the CMC cross-linked body having undergone Step (4). When the content of the foaming agent falls within the above range, CMC particles having excellent blood absorbency may be provided due to improved bulk density.

Also, in the first method, the surface cross-linker solution may include a hydrophilic volatile organic solvent as the solvent. Examples of the hydrophilic volatile organic solvent may include lower alcohols such as methanol, ethanol, n-propyl alcohol, isopropyl alcohol, n-butyl alcohol, isobutyl alcohol, tert-butyl alcohol, and the like; ketones such as acetone, methyl ethyl ketone, and the like; ethers such as 1,4-dioxane, tetrahydrofuran, and the like; amides such as N,N-dimethylformamide and the like; sulfoxides such as dimethyl sulfoxide, and the like. Specifically, the surface cross-linker solution may be an alcohol, and more specifically methanol, ethanol, or isopropyl alcohol.

According to one embodiment of the present invention, in the first method, Step (5) may be performed while stirring at 50° C. or higher and 90° C. or lower and at a speed of 100 rpm or higher and 300 rpm or less for 120 minutes or more and 270 minutes or less. When Step (5) is performed under the above reaction conditions, the foaming agent and the surface cross-linker may be uniformly distributed in the CMC cross-linked body, which results in improved surface cross-linking efficiency.

As a second method, Step (5) may be a secondary cross-linking step of surface cross-linking the carboxymethyl cellulose cross-linked body by adding a surface cross-linker solution, in which the surface cross-linker is dissolved in an organic solvent, and water to the carboxymethyl cellulose cross-linked body having undergone Step (4), and simultaneously obtaining gel-phase carboxymethyl cellulose by gelling the carboxymethyl cellulose cross-linked body.

According to one embodiment of the present invention, in the second method, the organic solvent may include a hydrophilic volatile organic solvent having a boiling point lower than water. Specifically, the organic solvent may include an alcohol having a boiling point lower than water. Examples of the hydrophilic volatile organic solvent having a boiling point lower than water may include lower alcohols such as methanol, ethanol, n-propyl alcohol, isopropyl alcohol, tert-butyl alcohol, and the like; ketones such as acetone and the like; ethers such as tetrahydrofuran and the like, and examples of the alcohol having a boiling point lower than water may include methanol, ethanol, isopropyl alcohol, or the like.

According to one embodiment of the present invention, in the second method, a content of the organic solvent added in Step (5) may be greater than or equal to 200 parts by weight and less than or equal to 2,000 parts by weight, based on 100 parts by weight of water. In Step (5) (a surface cross-linking step), the relative amounts of water and the organic solvent are very important. Specifically, when an amount of water is relatively larger than that of the organic solvent at the beginning of the surface cross-linking step, a rapid increase in viscosity caused by CMC swelling may be suppressed, and thus uniform surface cross-linking may be performed. Then, as a surface cross-linking reaction proceeds while the temperature is raised, the organic solvent may be evaporated such that an amount of the organic solvent may be relatively lower than that of water. As a result, the surface cross-linking reaction of the CMC cross-linked body having core cross-linking may proceed, and the CMC cross-linked body may be simultaneously swollen and hydrated in water, and then gelled.

According to one embodiment of the present invention, in the second method, Step (5) may include: stirring at a speed of 100 rpm or higher and 300 rpm or less for 120 minutes or more and 360 minutes or less while raising the temperature to greater than or equal to a "boiling point of the organic solvent" or an "azeotropic point of the organic solvent and water" and 100° C. or less. When Step (5) is performed under the above reaction conditions, the organic solvent having a boiling point lower than water may be first volatilized at the late stage of reaction. A uniform surface cross-linking reaction may proceed according to a change in solution balance between the organic solvent and water made during such a temperature raising process, and the CMC cross-linked body may be simultaneously gelled. As one example, when ethanol is used as the organic solvent, the solution balance at a temperature less than an azeotropic point (78.1° C.) of water and ethanol becomes "amount of organic solvent>amount of water." When the temperature is increased to a temperature greater than the azeotropic point, the solution balance may be changed to "amount of water>amount of organic solvent." That is, regular uniform surface cross-linking reaction mainly occurs at the beginning of the temperature raising process (amount of organic solvent>amount of water). When the change in solution balance is caused by the temperature increase (amount of water>amount of organic solvent), gelation may gradually proceed with the surface cross-linking reaction. As a result, because the gelation smoothly proceeds as the uniform surface cross-linking reaction proceeds, CMC having an excellent core-shell structure may be obtained. On the other hand, when CMC is cross-linked and simultaneously gelled in the presence of water alone without an organic solvent, the viscosity of CMC increases due to the rapid swelling of CMC at the early stage of reaction, which may result in irregular non-uniform cross-linking reaction.

(6) Obtaining CMC Particles

This step is a step of obtaining CMC particles having a core-shell structure by drying and pulverizing the CMC having a core-shell structure obtained in Step (5) to. In this case, the CMC having a core-shell structure may be dried and pulverized after a dehydration process.

Conventional drying methods known in the art may be used for the drying without any limitation. For example, a drying method such as natural drying, hot-air drying, or high-temperature drying may be used.

Also, the pulverization may be performed using a conventional pulverizer known in the art. For example, a cutting mill, a hammer mill, a pin mill, a screw mill, a roll mill, a disc mill, or the like may be used.

According to one embodiment of the present invention, CMC particles having a core-shell structure obtained in Step (6) may have a bulk density of 0.5 g/mL or more and 0.9 g/mL or less. In this case, the CMC particles having excellent blood absorbency and dispersibility may be provided. In particular, when the bulk density of the CMC particles falls within the above range, problems regarding a gel blocking phenomenon caused when the CMC particles float to an upper portion of an absorbent article including the CMC particles as the absorbent article absorbs a liquid, or regarding degraded initial absorbability caused when the CMC particles densely settle in a lower portion of the absorbent article may be resolved.

The method for manufacturing CMC particles according to the present invention may further include: a sorting step of sieving the porous CMC particles having a core-shell structure obtained in Step (6) to obtain CMC particles having a size of 150 μm or more and 850 μm or less. When the size of the CMC particles falls within the above range, problems regarding a gel blocking phenomenon caused due to degraded dispersibility due to a small size of the CMC particles, or regarding degraded absorbability caused by excessive permeability due to a large size of the CMC particles may be resolved. Considering dispersibility and absorbability together, the size of the CMC particles may be greater than or equal to 250 μm and less than or equal to 500 μm.

Another embodiment of the present invention provides CMC particles manufactured by the method for manufacturing CMC particles, and an absorbent article including the same.

According to one embodiment of the present invention, a blood absorbency of the CMC particles obtained according to the following Calculation Formula 1 may be greater than or equal to 130 mg and less than or equal to 155 mg:

$$\text{Blood absorbency (mg)} = W_2 - W_1 \quad \text{Calculation Formula 1}$$

$W_1$ represents a weight of a Petri dish, and $W_2$ represents a weight of the Petri dish measured after evenly scattering 1.0 g of the CMC particles on the Petri dish, continuously dropping 0.1 mL of blood in a dropwise manner in the center of the dish containing the CMC particles, allowing the blood to coagulate at room temperature for 2 hours, and sweeping off all the clean CMC particles which does not contact with the blood.

As such, the CMC particles manufactured according to the present invention may be preferably used in feminine sanitary pads which are feminine products for absorbing blood because the CMC particles have excellent AUL, CRC, and blood absorbency. In addition to the feminine products, the CMC particles may be used to manufacture absorbent articles selected from the group consisting of hygiene products such as disposable diapers, adult incontinence products, and the like; and pet supplies such as defecation pads and the like. Also, the CMC particles may widely be used as materials for medical absorbents, waterproofing materials for civil engineering and construction, sheets for raising seedlings, freshness retainers used in the field of food distribution; and the like.

Hereinafter, the present invention will be described in further detail with reference to examples. However, it should be understood that the following examples are not intended to limit the present invention.

Example 1

First, pulp (Rayonier Inc., Ethenier-F) was cut into pieces with a length of 0.15 mm or more and 0.5 mm or less to prepare a cellulose raw material.

Next, 90 g of the cut cellulose raw material was put into a pressure reactor (Lodige Industries GMBH, Druvatherm series), and 1,231 g of an aqueous solution including 80% by weight of isopropyl alcohol as a reaction solvent was added thereto. Thereafter, 158 g of an aqueous solution including 50% by weight of sodium hydroxide as an alkalizer was added thereto, and reacted while stirring at 25° C. and a speed of 150 rpm for 120 minutes to obtain alkalized cellulose.

Then, 360 g of an aqueous solution including 45% by weight of chloroacetic acid sodium salt as a carboxy methylating agent was put into the reactor to manufacture CMC. In this case, the CMC was manufactured through a primary carboxy methylation step of reacting alkalized cellulose with a carboxy methylating agent in the reactor while stirring at 50° C. and a speed of 200 rpm for 120 minutes, followed by a secondary carboxy methylation step of raising the temperature to 70° C. and allowing a reaction for 60 minutes. A degree of carboxymethyl group substitution (DS) of the CMC thus manufactured was 1.0, and a degree of polymerization (DP) of the CMC was 1,400.

Subsequently, 4 g of glycerol diglycidyl ether as a core cross-linker was put into a reactor containing the CMC, and a core cross-linking reaction (i.e., a primary cross-linking reaction) was carried out while stirring at 70° C. and a speed of 200 rpm for 60 minutes to manufacture a slurry-phase CMC cross-linked body. In this case, the CMC cross-linked body was not gelled.

Then, the slurry-phase CMC cross-linked body was discharged from the reactor, and filtered through a suction filter (LK Labkorea Co. Ltd., WJ-110). Thereafter, 900 g of an aqueous solution including 70% by weight of ethanol was added thereto to perform primary washing, and 900 g of an aqueous solution including 80% by weight of ethanol was added thereto to perform secondary washing. Then, the resulting mixture was dehydrated.

Subsequently, 30 g of the CMC cross-linked body having undergone the dehydration process was transferred back to the pressure reactor, and 270 g of a 1% polyethylene glycol diglycidyl ether solution (solvent: ethanol), and 90.45 g of an aqueous foaming agent solution in which 0.45 g of sodium bicarbonate (as a foaming agent) was dissolved in 90 g of water were added thereto. Thereafter, after an internal temperature of the reactor was increased to 70° C., the resulting mixture was subjected to a surface cross-linking reaction (i.e., a secondary cross-linking reaction) while stirring at 70° C. and a speed of 150 rpm for 180 minutes to manufacture porous CMC having a core-shell structure.

Then, after the surface cross-linking reaction was completed, the porous CMC having a core-shell structure was dehydrated, dried with hot air at 70° C. for 360 minutes, and then pulverized using a cutting mill (Fritsch GMBH, Pulverisette 19) to manufacture porous CMC particles (hereinafter referred to as "particles 1") having a core-shell structure. In this case, the particles 1 had a particle size in a range of 250 μm or more and 500 μm or less. Also, the particles 1 were obtained by sieving the CMC particles with a 60-mesh (250 μm) standard sieve to obtain CMC particles having a size of 250 μm or more, and then sieving the obtained CMC particles with a 35-mesh (500 μm) standard sieve to exclude particles having a size greater than 500 μm.

Example 2

CMC particles (hereinafter referred to as "particles 2") having a core-shell structure were manufactured in the same manner as in Example 1, except that 90.09 g of an aqueous foaming agent solution in which 0.09 g of sodium bicarbonate (as a foaming agent) was dissolved in 90 g of water was added.

Example 3

CMC particles (hereinafter referred to as "particles 3") having a core-shell structure were manufactured in the same manner as in Example 1, except that 90.27 g of an aqueous foaming agent solution in which 0.27 g of sodium bicarbonate (as a foaming agent) was dissolved in 90 g of water was added.

Example 4

CMC particles (hereinafter referred to as "particles 4") having a core-shell structure were manufactured in the same manner as in Example 1, except that 90.9 g of an aqueous foaming agent solution in which 0.9 g of sodium bicarbonate (as a foaming agent) was dissolved in 90 g of water was added.

Example 5

CMC particles (hereinafter referred to as "particles 5") having a core-shell structure were manufactured in the same manner as in Example 1, except that 94.5 g of an aqueous foaming agent solution in which 4.5 g of sodium bicarbonate (as a foaming agent) was dissolved in 90 g of water was added.

Example 6

CMC particles (hereinafter referred to as "particles 6") having a core-shell structure were manufactured in the same manner as in Example 1, except that the surface cross-linking reaction time was adjusted to 240 minutes.

Example 7

CMC particles (hereinafter referred to as "particles 7") having a core-shell structure were manufactured in the same manner as in Example 1, except that the secondary carboxy methylation reaction time was adjusted to 80 minutes.

Example 8

The ungelled slurry-phase CMC cross-linked body discharged from the reactor in Example 1 was filtered, washed, and dehydrated in the same manner as in Example 1.

Next, 30 g of the CMC cross-linked body having undergone the dehydration process was transferred back to the pressure reactor, and 270 g of a 1% polyethylene glycol diglycidyl ether solution (solvent: ethanol) and 90 g of water were added thereto. Thereafter, the resulting mixture was stirred at a speed of 150 rpm for 240 minutes while increasing an internal temperature of the reactor to 70° C., and then subjected to a surface cross-linking reaction (i.e., a secondary cross-linking reaction) and gelation at the same time to manufacture gel-phase CMC having a core-shell structure. In this case, an azeotropic point of ethanol and water as the solvent in the surface cross-linker solution was 78.1° C. In this case, an amount of ethanol in the reactor was larger than that of water at a temperature lower than the azeotropic point, and an amount of ethanol was smaller than that of water because the solution balance changes when the temperature is raised above the azeotropic point.

Subsequently, after the surface cross-linking reaction was completed, the gel-phase CMC was dehydrated and dried with hot air in the same manner as in Example 1, and then pulverized to manufacture CMC particles (hereinafter referred to as "particles 8") having a size of 250 µm or more and 500 µm or less and having a core-shell structure.

Example 9

CMC particles (hereinafter referred to as "particles 9") having a core-shell structure were manufactured in the same manner as in Example 8, except that, for a surface cross-linking reaction (i.e., a secondary cross-linking reaction), the mixture was stirred at a speed of 150 rpm for 300 minutes while increasing an internal temperature of the reactor to 88° C., and then subjected to a surface cross-linking reaction (i.e., a secondary cross-linking reaction) and gelation at the same time to manufacture gel-phase CMC having a core-shell structure.

Example 10

CMC particles (hereinafter referred to as "particles 10") having a core-shell structure were manufactured in the same manner as in Example 8, except that, before a core cross-linking reaction (i.e., a primary cross-linking reaction) proceeded after CMC was manufactured through the primary and secondary carboxy methylation steps, the reactor containing the CMC was cooled to a temperature of 30° C., and 60 mL of a 35% HCl solution was slowly added dropwise thereto for 20 minutes so that the mixture was neutralized to pH 8.5.

Comparative Example 1

CMC particles (hereinafter referred to as "particles 11") having a core-shell structure were manufactured in the same manner as in Example 1, except that 90 g of foaming agent-free water was added instead of the aqueous foaming agent solution.

Comparative Example 2

CMC particles (hereinafter referred to as "particles 12") having a core-shell structure were manufactured in the same manner as in Comparative Example 1, except that the surface cross-linking reaction time was adjusted to 240 minutes.

Comparative Example 3

CMC particles (hereinafter referred to as "particles 13") having a core-shell structure were manufactured in the same manner as in Comparative Example 1, except that the secondary carboxy methylation reaction time was adjusted to 80 minutes.

Comparative Example 4

The slurry-phase CMC cross-linked body discharged from the reactor in Example 8 was filtered, washed, and dehydrated in the same manner as in Example 8, and water was then added thereto. Thereafter, the resulting mixture was kneaded to obtain a CMC cross-linked body paste. In this case, an addition amount of water was 1,000 parts by weight, based on 100 parts by weight of the slurry-phase CMC cross-linked body having undergone the dehydration process.

Next, the CMC cross-linked body paste was molded into a spherical shape with a diameter of 2 cm, dried at 70° C. for 360 minutes in an oven, and then pulverized using a cutting mill (Fritsch GMBH, Pulverisette 19) to manufacture a granular CMC cross-linked body. In this case, the granular CMC cross-linked body had a particle size of 250 µm or more and 500 µm or less and had only core cross-linking.

Then, 30 g of the granular CMC cross-linked body was transferred back to the pressure reactor, and 90 g of water and 270 g of a 1% polyethylene glycol diglycidyl ether solution (solvent: ethanol) as a surface cross-linker solution were added thereto. Thereafter, the resulting mixture was subjected to a surface cross-linking reaction using an immersion method. In this case, the surface cross-linking reaction temperature was 70° C., and the reaction time was 1,440 minutes. Here, the immersion method refers to a method of performing surface cross-linking in a state in which the CMC cross-linked body is immersed in water and the polyethylene glycol diglycidyl ether solution without a stirring process.

After the surface cross-linking reaction was completed, the reaction mixture was dehydrated, dried, and pulverized in the same manner as in Example 8 to manufacture CMC particles (hereinafter referred to as "particles 14") having a core-shell structure.

Comparative Example 5

CMC particles (hereinafter referred to as "particles 15") having a core-shell structure were manufactured in the same manner as in Comparative Example 4, except that pulp (having a length of 8 mm or more), which was not cut into the cellulose raw material, was used, and the reaction time in the primary carboxy methylation step was adjusted to 180 minutes, and the reaction time in the secondary carboxy methylation step was adjusted to 120 minutes.

Comparative Example 6

CMC was subjected to a core cross-linking reaction and washing and dehydration processes in the same manner as in Comparative Example 4 to manufacture a CMC cross-linked body having core cross-linking, except that pulp (having a length of 8 mm or more), which was not cut into the cellulose raw material, was used, and the reaction time in the primary carboxy methylation step was adjusted to 180 minutes, and the reaction time in the secondary carboxy methylation step was adjusted to 120 minutes.

Next, the CMC cross-linked body having undergone the dehydration process was directly dried with hot air at 70° C. for 360 minutes without a surface cross-linking step, and then pulverized using a cutting mill (Fritsch GMBH, Pulverisette 19) to manufacture CMC particles (hereinafter referred to as "particles 16") having only core cross-linking.

Evaluation Method

1. Blood Absorbency

The blood absorbency of each of the particles 1 to 16 obtained in Examples 1 to 10 and Comparative Examples 1 to 6 was evaluated, as follows.

First, a weight of a Petri dish having an inner diameter of 3 cm was measured, and 1.0 g of the particles were scattered on the Petri dish. Thereafter, the bottom of the Petri dish was tapped so that the particles were evenly spread on a surface of the Petri dish. Then, 0.1 mL of blood was put into a 1 mL plastic syringe, and a 21 G needle was mounted on the plastic syringe. Subsequently, the blood was continuously and slowly dropped drop-by-drop on the center of the particles contained in the Petri dish. In this case, the blood of a horse was used as the blood. Then, the blood was coagulated at room temperature for 2 hours, and all the clean particles which did not contact with the blood were swept off. Then, a weight ($W_2$) of the Petri dish containing the coagulated blood and the particles congealed with the blood was measured. The blood absorbency was calculated according to the following Equation 1 using the measured weight. The results are listed in Table 1 below.

$$\text{Blood absorbency (mg)} = W_2 - W_1 \qquad \text{[Equation 1]}$$

wherein $W_1$ represents a weight of an empty Petri dish, and $W_2$ represents a weight of the Petri dish containing the coagulated blood and the particles congealed with the blood.

Specifically, FIG. 1 is an image of CMC particles manufactured in Example 1 to which blood is applied, and FIG. 2 is an image of the CMC particles after the CMC particles which does not contact with blood are swept off from the Petri dish shown in FIG. 1. Also, FIG. 3 is an image of CMC particles manufactured in Example 8 to which blood is applied, and FIG. 4 is an image of the CMC particles after the CMC particles which does not contact with blood are swept off from the Petri dish shown in FIG. 3.

2. Absorbency Under Load (AUL)

The absorbency under load of each of the particles 1 to 16 obtained in Examples 1 to 10 and Comparative Examples 1 to 6 was measured using a device shown in FIG. 5.

First, a 400-mesh metal mesh 5 was mounted on the bottom of a circular polymethyl methacrylate (PMMA) cylinder 7 (inner diameter: 60 mm and height: 50 mm). 0.9 g ($W_3$) of the particles 6 were evenly placed on the metal mesh 5 at room temperature, and a plastic piston 8 equipped with a 0.7-psi metal weight 9 was placed on the metal mesh 5 to configure an AUL measurement device.

Next, a glass ceramic filter plate 2 of porosity #0 (diameter: 80 mm and thickness: 7 mm) was placed inside a Petri dish 1 (diameter: 118 mm and height: 12 mm), and physiological saline 3 composed of an aqueous 0.9% sodium chloride solution was added thereto so that the physiological saline 3 was flush with the ceramic filter plate 2. Thereafter, a filter paper 4 was placed on the ceramic filter plate 2.

Then, the AUL measurement device was placed on the filter paper 4, and the particles were allowed to absorb physiological saline under pressure for 60 minutes. Thereafter, a weight ($W_4$) of the particles in the measurement device was measured. The AUL was measured according to the following Equation 2 using the weight thus measured. The results are listed in Table 1 below.

$$\text{AUL (g/g)} = (W_4 - W_3)/W_3 \qquad \text{[Equation 2]}$$

wherein $W_3$ represents an initial weight (0.9 g) of the particles, and $W_4$ represents a weight of the particles after the particles are allowed to absorb physiological saline for 60 minutes under pressure (0.7 psi).

3. Centrifuge Retention Capacity (CRC)

The centrifuge retention capacity of each of the particles 1 to 16 obtained in Examples 1 to 10 and Comparative Examples 1 to 6 was measured, as follows.

0.2 g ($W_5$) of each of the particles was uniformly put into a tea bag, and the tea bag was hermetically sealed. Thereafter, the tea bag was immersed in physiological saline composed of an aqueous 0.9% sodium chloride solution at room temperature for 30 minutes. Then, the hermetically sealed tea bag was centrifuged at 250 G for 3 minutes using a centrifuge to remove moisture from the hermetically sealed tea bag, and a weight ($W_6$) of the hermetically sealed tea bag was measured. In addition, a tea bag which did not contain the particles was also subjected to the same immersion and centrifugation processes, and a weight ($W_7$) of the hermetically sealed tea bag was measured. The CRC was calculated according to the following Equation 3 using the weights thus measured. The results are listed in Table 1 below.

$$CRC\ (g/g)=(W_6-W_7-W_5)/W_5 \quad \text{[Equation 3]}$$

wherein $W_5$ represents an initial weight (0.2 g) of the particles, $W_6$ represents a weight of a hermetically sealed tea bag containing the particle after the hermetically sealed tea bag is immersed and centrifuged, and $W_7$ represents a weight of a tea bag which does not contain the particle after the tea bag is immersed and centrifuged.

TABLE 1

|  | AUL (g/g) | CRC (g/g) | Blood absorbency (mg) |
|---|---|---|---|
| Example 1 | 9.51 | 33.0 | 150 |
| Example 2 | 9.46 | 32.7 | 133 |
| Example 3 | 9.48 | 32.8 | 140 |
| Example 4 | 9.50 | 33.0 | 151 |
| Example 5 | 9.50 | 33.2 | 151 |
| Example 6 | 9.51 | 32.9 | 150 |
| Example 7 | 9.51 | 32.9 | 149 |
| Example 8 | 9.51 | 32.2 | 148 |
| Example 9 | 9.52 | 33.1 | 153 |
| Example 10 | 9.51 | 32.7 | 150 |
| Comparative Example 1 | 9.41 | 31.5 | 123 |
| Comparative Example 2 | 9.42 | 31.0 | 123 |
| Comparative Example 3 | 9.42 | 31.4 | 122 |
| Comparative Example 4 | 9.42 | 30.9 | 124 |
| Comparative Example 5 | 9.39 | 31.3 | 120 |
| Comparative Example 6 | 8.38 | 30.5 | 75 |

As shown in Table 1, it can be seen that the particles 1 to 10 manufactured in Examples 1 to 10 had superior AUL, CRC, and blood absorbency, compared to the particles 11 to 16 manufactured in Comparative Examples 1 to 6. In particular, it can be seen that the particles 1 to 10 had remarkably excellent blood absorbency.

As described above, it should be understood that the embodiments disclosed in the present invention are merely illustrative of the present invention in detail and are not intended to limit the scope of the present invention. Accordingly, it should be interpreted that the scope of the present invention is defined by the appended claims, and intended to encompass all modifications and changes falling within the meaning and the scope of the appended claims, and any equivalents thereof.

BRIEF DESCRIPTION OF MAJOR PARTS IN DRAWINGS

1: Petri dish
2: ceramic filter plate
3: physiological saline (or NaCl solution)
4: filter paper
5: metal mesh
6: absorbent particle (or superabsorbent particles)
7: PMMA cylinder
8: plastic piston
9: metal weight

The invention claimed is:

1. A method for manufacturing carboxymethyl cellulose particles, comprising:
   (1) a step of obtaining alkalized cellulose by reacting a cellulose raw material with an alkalizer;
   (2) a step of obtaining carboxymethyl cellulose by reacting the alkalized cellulose with a carboxy methylating agent;
   (3) a primary cross-linking step of obtaining a slurry-phase carboxymethyl cellulose cross-linked body by reacting the carboxymethyl cellulose with a core cross-linker;
   (4) a step of washing and dehydrating after filtering the slurry-phase carboxymethyl cellulose cross-linked body;
   (5) a secondary cross-linking step of obtaining carboxymethyl cellulose having a core-shell structure by reacting the carboxymethyl cellulose cross-linked body having undergone Step (4) with a surface cross-linker; and
   (6) a step of obtaining carboxymethyl cellulose particles having a core-shell structure by drying and pulverizing the carboxymethyl cellulose having a core-shell structure.

2. The method of claim 1, wherein the cellulose raw material is prepared by cutting one or more types of pulp selected from the group consisting of raw cotton, linter, and wood into a length of 0.15 mm or more and 0.5 mm or less.

3. The method of claim 1, wherein Step (2) comprises: (2-1) a primary carboxy methylation step performed at 40° C. or higher and 55° C. or lower for 90 minutes or more and 150 minutes or less; and (2-2) a secondary carboxy methylation step performed at 65° C. or higher and 75° C. or lower for 30 minutes or more and 90 minutes or less.

4. The method of claim 1, wherein a degree of carboxymethyl group substitution (DS) of the carboxymethyl cellulose manufactured in Step (2) is greater than or equal to 0.7 and less than or equal to 2.0, and a degree of polymerization (DP) of the carboxymethyl cellulose is greater than or equal to 800 and less than or equal to 4,000.

5. The method of claim 1, further comprising, before undergoing Step (3): (2.5) neutralizing the carboxymethyl cellulose obtained in Step (2).

6. The method of claim 1, wherein the core cross-linker comprises one or more selected from the group consisting of an epoxy compound and a polyhydric alcohol.

7. The method of claim 1, wherein a content of the core cross-linker is greater than or equal to 0.1 parts by weight and less than or equal to 40 parts by weight, based on 100 parts by weight of the cellulose raw material.

8. The method of claim 1, wherein Step (3) is performed at 65° C. or higher and 75° C. or lower while stirring at a speed of 100 rpm or higher and 300 rpm or less for 30 minutes or more and 90 minutes or less.

9. The method of claim 1, wherein one or more selected from the group consisting of water and a hydrophilic volatile organic solvent is used for washing in Step (4).

10. The method of claim 1, wherein the surface cross-linker comprises one or more selected from the group consisting of a polyhydric epoxy compound and a polyhydric alcohol.

11. The method of claim 1, wherein a content of the surface cross-linker is greater than or equal to 0.1 parts by weight and less than or equal to 40 parts by weight, based on 100 parts by weight of the carboxymethyl cellulose cross-linked body having undergone Step (4).

12. The method of claim 1, wherein Step (5) is a secondary cross-linking step of obtaining porous carboxymethyl cellulose having a core-shell structure by reacting the carboxymethyl cellulose cross-linked body having undergone Step (4) with the surface cross-linker and a foaming agent.

13. The method of claim 12, wherein the foaming agent comprises one or more carbonate compounds selected from the group consisting of magnesium carbonate, calcium carbonate, sodium bicarbonate, and potassium bicarbonate.

14. The method of claim 12, wherein a content of the foaming agent is greater than or equal to 0.03 parts by weight and less than or equal to 20 parts by weight, based on 100 parts by weight of the carboxymethyl cellulose cross-linked body having undergone Step (4).

15. The method of claim 12, wherein Step (5) is performed at 50° C. or higher and 90° C. or lower while stirring at a speed of 100 rpm or higher and 300 rpm or less for 120 minutes or more and 270 minutes or less.

16. The method of claim 1, wherein Step (5) is a secondary cross-linking step of surface cross-linking the carboxymethyl cellulose cross-linked body by adding a surface cross-linker solution, in which the surface cross-linker is dissolved in an organic solvent, and water to the carboxymethyl cellulose cross-linked body having undergone Step (4), and simultaneously obtaining gel-phase carboxymethyl cellulose by gelling the carboxymethyl cellulose cross-linked body.

17. The method of claim 16, wherein the organic solvent comprises a hydrophilic volatile organic solvent having a boiling point lower than water.

18. The method of claim 16, wherein the organic solvent comprises an alcohol having a boiling point lower than water.

19. The method of claim 16, wherein a content of the organic solvent added in Step (5) is greater than or equal to 200 parts by weight and less than or equal to 2,000 parts by weight, based on 100 parts by weight of water.

20. The method of claim 16, wherein Step (5) comprises:
stirring at a speed of 100 rpm or higher and 300 rpm or less for 120 minutes or more and 360 minutes or less while raising the temperature to greater than or equal to a "boiling point of the organic solvent" or an "azeotropic point of the organic solvent and water" and 100° C. or less.

21. The method of claim 1, wherein the carboxymethyl cellulose particles obtained in Step (6) have a bulk density of 0.5 g/mL or more and 0.9 g/mL or less.

22. Carboxymethyl cellulose particles manufactured by the method for manufacturing carboxymethyl cellulose particles defined in claim 1.

23. The carboxymethyl cellulose particles of claim 22, wherein a blood absorbency of the carboxymethyl cellulose particles obtained according to the following Calculation Formula 1 is greater than or equal to 130 mg and less than or equal to 155 mg:

$$\text{Blood absorbency (mg)} = W_2 - W_1 \qquad \text{Calculation Formula 1}$$

wherein $W_1$ represents a weight of a Petri dish, and $W_2$ represents a weight of the Petri dish measured after evenly scattering 1.0 g of the carboxymethyl cellulose particles on the Petri dish, continuously dropping 0.1 mL of blood in a dropwise manner in the center of the dish containing the carboxymethyl cellulose particles, allowing the blood to coagulate at room temperature for 2 hours, and sweeping off all the clean carboxymethyl cellulose particles which does not contact with the blood.

24. An absorbent article comprising carboxymethyl cellulose particles manufactured by the method for manufacturing carboxymethyl cellulose particles defined in claim 1.

* * * * *